(12) United States Patent
Cederholm-Williams

(10) Patent No.: US 6,492,494 B1
(45) Date of Patent: Dec. 10, 2002

(54) METHOD OF MAKING A FIBRIN SEALANT COMPRISING ALPHA-2-ANTIPLASMIN

(75) Inventor: Stewart A. Cederholm-Williams, Oxford (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/208,352

(22) Filed: Dec. 9, 1998

Related U.S. Application Data

(60) Provisional application No. 60/069,652, filed on Dec. 9, 1997.

(51) Int. Cl.$^7$ ............................................... A61K 35/14
(52) U.S. Cl. .................... 530/381; 530/382; 424/94.64; 435/214; 435/217
(58) Field of Search ..................... 514/12, 21; 435/212; 530/381, 382; 424/529, 530, 682, 94.64

(56) References Cited

U.S. PATENT DOCUMENTS

| | | | | |
|---|---|---|---|---|
| 5,750,657 A | * | 5/1998 | Edwardson et al. | 530/382 |
| 5,763,410 A | * | 6/1998 | Edwardson et al. | 514/21 |
| 5,773,418 A | * | 6/1998 | Edwardson et al. | 514/21 |

FOREIGN PATENT DOCUMENTS

| EP | 0592242 | 4/1994 |
|---|---|---|

OTHER PUBLICATIONS

Lee et al. Purification of human alpha 2–antiplasmin with chicken IgY specific to its carboxy–terminal peptide. Preparative Biochemistry & Biotechnology. 1997, vol. 27, No. 4, pp. 227–237.

Wiman, B. Affinity–chromatographic purification of human alph 2–antiplasmin. Biochem. J. 1980, vol. 191, No. 1, pp. 229–232.

Letters to the Editor and Replay to the Editor, J Thoracic and Cardiovascular Surgery, vol. 116, No. 8, Dec. 1998, pp. 1082–1083.

* cited by examiner

*Primary Examiner*—Sandra E. Saucier
(74) *Attorney, Agent, or Firm*—Theodore R. Furman, Jr.; John M. Kilcoyne

(57) ABSTRACT

The invention provides a kit for preparing a fibrin sealant either (A) comprising: (a) a fibrin monomer preparation; (b) a stabilizing preparation containing a clot-preserving effective amount of a fibrinolysis-inhibiting protein; and (c) a non-enzymatic polymerizing agent preparation effective to convert the fibrin monomer preparation into a fibrin clot; or (B) comprising: (a') a fibrin monomer preparation comprising a fibrin monomer and a clot-preserving effective amount of a of a fibrinolysis-inhibiting protein; and (c') a polymerizing agent preparation effective to convert the fibrin monomer preparation into a fibrin clot.

10 Claims, 3 Drawing Sheets

METHOD OF MAKING A FIBRIN SEALANT COMPRISING ALPHA-2-ANTIPLASMIN

The application claims benefit to U.S. provisional application Ser. No. 60/069,652, filed Dec. 9, 1997.

The present invention is directed to a fibrin sealant containing a fibrinolytic inhibitor, a method of isolating such a fibrinolytic inhibitor, and a device that isolates such a fibrinolytic inhibitor through an automated process utilizing centrifugal force.

"Fibrin" sealants are widely used to reduce bleeding in surgery and to seal blood vessels and tissues that have been dissected either in surgery or through wounding. The term "fibrin" can be viewed as a misnomer in this context since historically "fibrin" sealants have been delivered as a material containing the precursor of fibrin, namely fibrinogen. In such sealants, fibrinogen material has been co-delivered at the site to be sealed with a proteinase enzyme that converts the fibrinogen to fibrin. Once a sufficient amount of fibrin is formed from the fibrinogen, the fibrin spontaneously polymerizes into a fibrin polymer which—when sufficient polymer is assembled—forms a fibrin clot. Generally, the conversion enzyme has been bovine thrombin. Recently, however, an effective sealant has been described that delivers fibrin, in a "fibrin monomer" form that is stabilized against polymerization, to the site that is to be sealed. At the site, the stabilization conditions are reversed, and an effective clot forms. See, Edwardson et al., European Patent Application No. EP 592,242.

One of the particular advantages of this fibrin monomer sealant of EP 592,242 is that the sealant can be rapidly prepared from a small amount of a patient's blood only minutes before surgery, and this can be done using standard laboratory equipment. Processes for deriving the fibrinogen material of prior art sealants are much more demanding and more difficult to automate. Specialized tools for preparing fibrin monomer have also recently been described, and these tools allow an autologous sealant to be prepared from a patient in a rapid, highly reproducible, highly reliable, and highly safe manner. See, Holm, "Centrifuge Reagent Delivery System", WO 96/16713, Holm et al., "Method and Device for Separating Fibrin I from Blood Plasma", WO 96/16714 and Holm, "Centrifuge with Annular Filter", WO 96/16715. These patent applications describe a molded apparatus that operates in a centrifuge. A first chamber of the apparatus is filled with blood, and a centrifugation process separates the plasma from a pelleted cellular blood fraction. The plasma is transferred to a second chamber into which a conversion enzyme, which is covalently bound to biotin, is inserted. The enzyme operates to convert the fibrinogen in the plasma to fibrin, which fibrin molecules bond to one another to form polymers that precipitate to form a solid. The fibrin precipitate is pelleted by centrifugation, and the remaining plasma is transferred back to the first chamber. The pelleted fibrin precipitate is dissolved with a solubilizing liquid, which is most often an aqueous solution buffered at an acidic pH. The viscous fibrin monomer solution is mixed with agarose beads having bound avidin to remove traces of biotinylated conversion enzyme, and then washed into a third chamber (for example, a syringe) through a filter which removes the agarose beads. The retained agarose contains any residual enzyme bound via the high-affinity avidin-biotin interaction. The solubilized fibrin monomer composition can be used as a sealant as described in Edwardson et al., EP 592,242.

These improvements, thus, allow for an autologous sealant to be prepared in a rapid, automated process, and the autologous sealant so prepared is free of extrinsic proteinase enzymes such as bovine thrombin. However, if so prepared, the sealant does not contain quantities of inhibitors against fibrinolysis. These inhibitors can limit the rate, after the sealant has been used to form a fibrin clot, at which the body's housekeeping enzymes remove clotted fibrin. Aprotinin, a 6200 molecular weight polypeptide isolated from bovine lung, is one such fibrinolytic inhibitor. Bovine aprotinin could, of course, be added to the above-described sealant, but this would partially undermine one of the substantial advantages of the sealant, which advantage is the ability to prepare the sealant autologously so that the sealant and clot formed with the sealant contain only biopolymers that are derived from the patient. In fact, the repeated use in a patient of bovine aprotinin has been associated with adverse consequences such as hypersensitive reactions. Thus, what is needed in the art is a method of easily preparing from the species to be treated, most preferably the patient him or herself, a suitable inhibitor of fibrinolysis. In particular, what is needed is a method that can be coordinated with the automated process described above.

SUMMARY OF THE INVENTION

The invention provides a kit for preparing a fibrin sealant, wherein the kit is a first kit (A) comprising: (a) a fibrin monomer preparation; (b) a stabilizing preparation containing a clot-preserving effective amount of a fibrinolysis-inhibiting protein; and (c) a non-enzymatic polymerizing agent preparation effective to convert the fibrin monomer preparation into a fibrin clot; or a second kit (B) comprising: (a') a fibrin monomer preparation comprising a fibrin monomer and a clot-preserving effective amount of a fibrinolysis-inhibiting protein, and (c') a polymerizing agent preparation effective to convert the fibrin monomer preparation into a fibrin clot. Preferably, the fibrin-clot stabilizing effective amount is: (i) in a stabilizing preparation that is a solution, at least about 70 $\mu$g/ml alpha-2-antiplasmin, (more preferably 200 $\mu$g/ml, still more preferably 400 $\mu$g/ml); or (ii) in a stabilizing preparation that is a solid, at least about 70 mg alpha-2-antiplasmin per g of fibrin, (more preferably 120 mg per g, still more preferably 30 mg per g. Preferably, the fibrin monomer preparation is a liquid and the concentration of fibrin monomer in the preparation is at least about 8 mg/ml (more preferably 15 mg/ml, still more preferably 30 mg/ml). Preferably, the fibrin monomer preparation comprises a fibrin-solubilizing effective amount of acid and the polymerizing agent preparation comprises an amount of base sufficient to bring the amount of acid to less than a fibrin-solubilizing effective amount or the fibrin monomer preparation comprises a fibrin monomer lyophilizate and the polymerizing agent preparation comprises an aqueous buffer.

The invention also provides a method of forming a fibrin sealant from an animal comprising: (a) contacting a first extract from the animal containing a fibrinolysis-inhibiting protein with a clot inhibitor-binding ligand bound to an extraction implement; (b) isolating a first composition comprising a fibrinolysis-inhibiting protein; (c) contacting a second extract from the animal, which contains fibrinogen and which can be the same as the first extract, with a fibrinogen-converting enzyme; and (d) isolating a second composition comprising a clot-forming effective amount of fibrin monomer from the contacted second extract, wherein the amount of isolated fibrinolysis-inhibiting protein is sufficient to stabilize at least a clot-forming effective amount of the second composition. Preferably, the first and second extracts are the same, and the first extract is blood or a blood derivative.

The method can further comprise (1) sealing a tissue to prevent fluid loss or to prevent adhesions to the tissue or (2) coating a material to increase its biocompatibility by: (e) contacting the second composition with a polymerizing agent composition effective to convert the fibrin monomer preparation into a fibrin clot; and (f) further contacting the second composition with a clot preserving effective amount of the first composition.

DEFINITIONS

Figure 1:
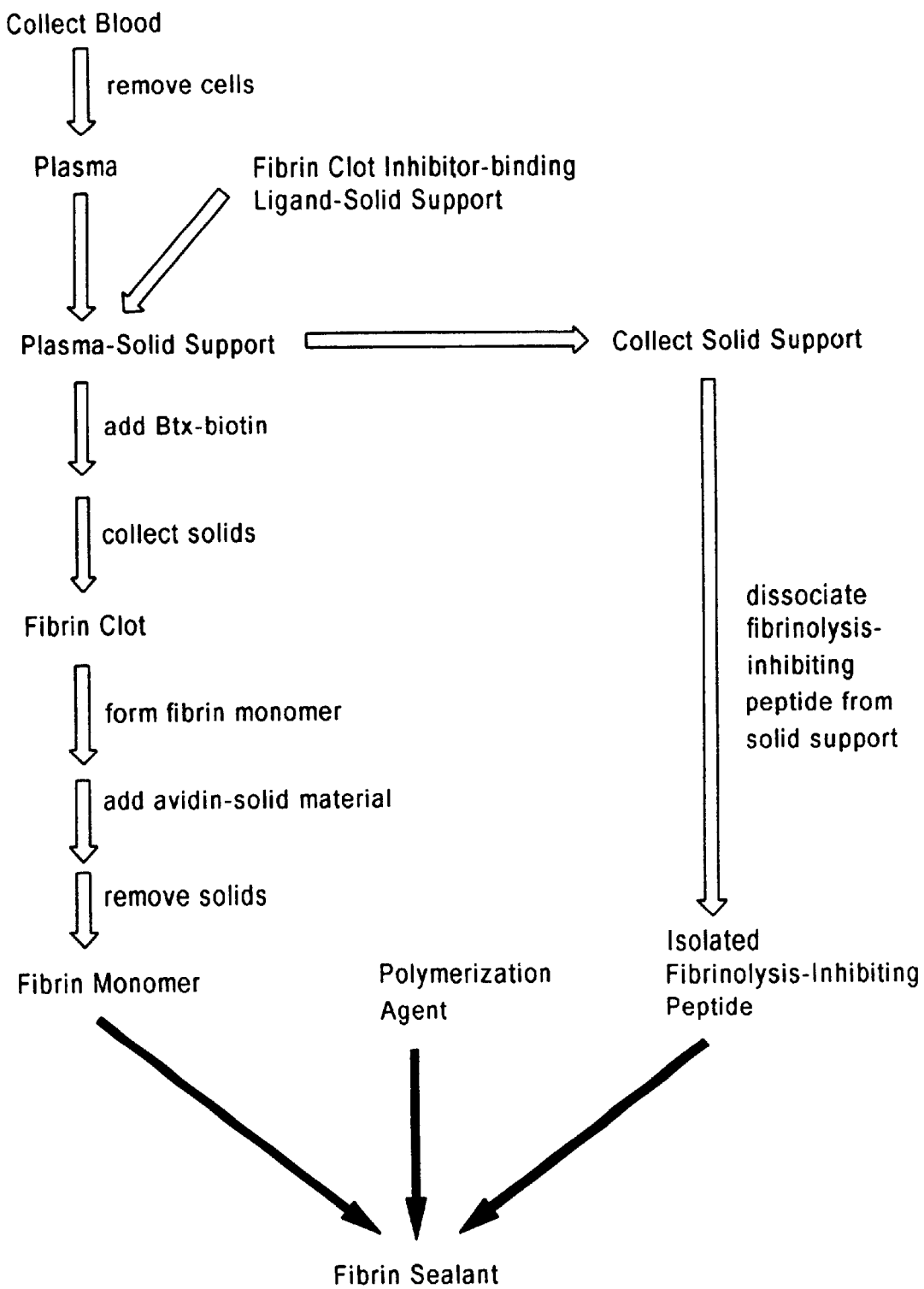
FIG. 1 shows an outline of a procedure for preparing a fibrin sealant containing an autologous fibrinolytic inhibitor, where the inhibitor is removed from the plasma prior to polymerizing fibrin.

For the purposes of this application, the following terms will have the meaning set forth below.

Extraction Implement

"Extraction implement" is a structure that facilitates the removal from solution of molecules bound thereto. Extraction implements include without limitation solids or larger molecules that can be removed by sedimentation or filtration (including ultrafiltration), members of binding pairs where the other member of a binding pair can be used to extract the first binding pair from a solution, and charged or magnetic particles that can be extracted using electrical or magnetic fields.

Fibrin

One of a number of derivatives of fibrinogen {e.g., fibrin I (i.e., desAA-fibrin), fibrin II (i.e., desAAdesBB fibrin) or des BB fibrin} that can polymerize to form a precipitate of fibrin polymer. The derivatives are created by cleaving the A or B fibrinopeptides from fibrinogen.

Fibrin Clot-forming Effective Amount

An effective amount of clot-forming fibrin is that quantity or concentration (if in a liquid form) of a fibrin (for example fibrin monomer) which forms sufficient clot material to be of utilized as a fibrin sealant.

Fibrin-clot-preserving Effective Amount

An effective amount of fibrinolytic inhibitor is that quantity of alpha-2-antiplasmin or other fibrinolysis-inhibiting protein which when added to fibrin increases the time that a fibrin clot remains in or on a tissue as an effective fibrin sealant.

Fibrin Monomer

Fibrin monomer is fibrin that is held in soluble form and prevented from clotting, for instance by the presence of a polymerization inhibitor such as acidic pH or a chaotropic agent or by being kept in a form which prevents polymerization, such as a sufficiently dehydrated form or a frozen form. Another form of fibrin monomer is an engineered version of fibrin which will not self-polymerize, but will polymerize with another fibrin-related molecule such as fibrinogen. Such an engineered fibrin is described in Cederholm et al., "Recombinant Fibrin Chains, Fibrin and Fibrin-Homologs," PCT Application No. PCT/US95/05527, filed May 2, 1995.

Fibrin Polymer

Fibrin molecules, in the absence of conditions that prevent polymerization of fibrin monomer, interact noncovalently to form polymers, here termed "fibrin polymers", which—when sufficient mass is achieved—form a visible adherent precipitate with clot-like properties. By the action of factor $XIII^a$, fibrin polymer can be covalently crosslinked. Prior to the crosslinking action of factor $XII^a$, fibrin polymer can be reversibly converted to fibrin monomer. Even when some initial such crosslinking has occurred, it is believed that fibrin polymer can be reversibly converted to fibrin monomer.

Fibrinolysis-inhibiting Protein

A fibrinolysis-inhibiting protein is a polypeptide found in a mammalian body fluid, or a polypeptide derived from such a mammalian polypeptide, that when infused or otherwise incorporated into a fibrin clot increases the time that the fibrin clot—when in contact with a tissue having plasmin or plasminogen—remains effective in, for example, binding tissues together, limiting body fluid leakage, preventing tissue adhesions or increasing the biocompatibility of a material. Examples of fibrinolysis-inhibiting proteins include alpha-2-antiplasmin, alpha-2-macroglobin and aprotinin.

High Affinity Binding High affinity binding between a first substance and a second substance is binding of sufficient avidity to allow for the first or second substance to be used as an affinity ligand for the isolation of the other substance. Typically, high affinity binding is reflected in an association constant of about $10^5$ $M^{-1}$ or more, preferably $10^6$ $M^{-1}$ or more, yet more preferably $10^7$ $M^{-1}$ or more.

DETAILED DESCRIPTION OF THE INVENTION

After the conversion from fibrinogen to fibrin, the fibrin rapidly polymerizes through noncovalent interactions such as hydrogen bonds, ionic bonds, hydrophobic interactions and Van der Waals interactions. The polymerized fibrin forms a clot. The clot can mature through the formation of covalent crosslinks under the direction of the active form of factor XIII, which is a transglutaminase enzyme called factor $XIII^a$. The prevention of unwanted occlusions of blood vessels by fibrin clots is believed to be done by a proteolytic enzyme called plasmin. Plasmin is formed, in a highly regulated process, from a precursor called plasminogen.

Blood contains inhibitors of plasmin, including alpha-2-macroglobulin and alpha-2-antiplasmin ("AP"). Alpha-2-antiplasmin is believed to be the primary inhibitor of plasmin in the blood. See, Aoki et al., *J Clin. Invest.* 60: 361, 1977, and Collen and Wiman, *Blood* 51: 563–569, 1978. The reaction between AP and plasmin occurs in two steps, with the first being a rapid, reversible interaction (rate constant of the order of $10^7$ mol/sec), and the second being a slower intra-molecular rearrangement that results in the formation of a covalent bond between alpha-2-antiplasmin and plasmin (rate constant of the order of $10^5$ mol/sec). At clotting sites, alpha-2-antiplasmin becomes covalently attached to fibrin via activity of the same enzyme, factor $XIII^a$, that crosslinks fibrin polymer.

As mentioned above, the fibrin composition described in European Patent Application No. 592,242, is made up of fibrin that is prevented from polymerization, i.e., fibrin monomer. Most often this polymerization prevention is achieved by solubilizing the fibrin in an aqueous solution having pH of about 4. To form a clot that can be used in surgery to minimize body fluid loss or to bond tissues together, the polymerization prevention conditions are reversed, which results in the rapid formation of fibrin polymer precipitate. Generally, polymerization prevention is reversed by neutralizing the acidity of the fibrin composition at the same time the composition is being sprayed onto the site where clot formation is intended.

For use as a sealant in surgery and other applications, the fibrin composition described in European Patent Application No. 592,242 can usefully contain an inhibitor of plasmin driven fibrinolytic housekeeping functions, such as the inhibitors aprotinin, alpha-2-antiplasmin or alpha-2-macroglobulin. Such inhibitors increase the residence time of the resulting clot when the sealant is applied to tissues with high fibrinolytic activity such as prostate. However, consistent with the concept that drove the development of the EP 592,242 sealant, such an inhibitor is preferably easily isolated from blood in a rapid method that would allow the sealant composition to have all of its active components derived from the patient to which the sealant will be applied. The method preferably should also be readily adaptable to an automated process such as is available through the apparatuses described in Holm, WO 96/16713, Holm et al., WO 96/16714 and Holm, WO 96/16715. The method should further isolate the fibrinolytic inhibitor in sufficient concentration to provide a useful fibrinolytic inhibitor function to the fibrin sealant. The present invention provides such a method, as described further in the Summary of the Invention and the text below.

A. Ligands that Bind Fibrinolvsis-inhibiting Proteins

Alpha-2-antiplasmin binds to plasminogen, and particularly it binds to one or more of the so-called "Kringle" domains of plasminogen, which are binding domains found in a number of proteins involved in coagulation or fibrinolysis. These Kringle domains consist of approximately 80-amino acid sequences, each with three disulfide bonds in conserved locations. Hoover et al., *Biochemistry* 32: 10936–10943, 1993. These sequences can be used as the basis for procedures to identify other ligands that bind to alpha-2-antiplasmin, as described further below. AP-binding ligands can also be prepared by digesting plasminogen or plasmin with a proteinase, such as elastase or chymotrypsin, that can destroy plasmin's enzymatic activity, while preserving the alpha-2-antiplasmin-binding activity. Such proteinase digestion products can be used directly without purification, or a purification procedure can be applied to isolate fractions with binding activity. Additional AP-binding ligands can be identified by the methods described below or other protein chemistry or molecular biology techniques known to the art.

Additional affinity ligands that can be used to isolate fibrinolysis-inhibiting proteins such as alpha-2-antiplasmin and alpha-2-macroglobin include appropriate monoclonal and polyclonal antibodies, dyes, and chelated zinc ions.

B. Purification Methods Generally

1. Solid Support Embodiments

FIG. 1 outlines how ligands that bind fibrinolytic-inhibitors can be used to isolate fibrinolysis-inhibiting protein and particularly how to isolate such polypeptides together with fibrin monomer.

First, blood is collected and a plasma is isolated therefrom. The blood can be mixed with an anticoagulant, such as trisodium citrate to a final concentration of about 0.5% w/v, and the plasma can be isolated by centrifugation, which removes the cellular components of the blood. A solid support having a bound ligand that binds to a fibrinolysis-inhibiting protein is mixed with the plasma to bind a fibrinolysis-inhibiting protein found in the plasma. In one embodiment of the invention, the solid support is separated from the plasma. The solid support can be washed with a solution designed to remove macromolecules found in the fluid removed with the solid support or non-specifically bound to the solid support. For example, the solid support can be washed with an aqueous buffer having a substantially neutral pH, such as a pH between about 6 and about 8, and an ionic strength between about 0.05 M and about 0.3 M. All or part of the washes (for example, the initial wash) can be mixed with the plasma, which is then further processed to isolate fibrin monomer.

More specifically, where monoclonal antibodies are utilized, the conditions for associating the antibody and fibrinolysis-inhibiting protein will vary with the characteristics of the antibody. These characteristics can be identified through standard experimentation. Where polyclonals are utilized, dissociation conditions often can be low pH, such as a pH of about 2.5. If low pH is used, care is taken to minimize the time to which the fibrinolysis-inhibiting protein is exposed to the low pH. For dye binding, dissociation is typically effected with elevated ionic strength solutions. Zinc chelation is more applicable to the post-polymerization embodiment of FIG. 2 (discussed below), since fibrinogen exhibits competing binding to zinc, which competing binding makes it preferably to use zinc binding after the serum is fibrin depleted.

The solid support is then eluted using conditions, such as are described further below, for destabilizing the interaction between the ligand and the fibrinolysis-inhibiting protein. After the fibrinolysis-inhibiting protein is eluted, the buffer can be exchanged for a buffer suitable for use as a fibrinolytic inhibitor of a fibrin sealant or suitable for processing by lyophilization.

Added to the plasma is an enzyme that converts fibrinogen to fibrin. In converting fibrinogen to fibrin, care preferably is taken to prevent the formation of crosslinks between fibrin molecules via the transaminase activity of factor $XIII^a$. This can be done by a number of techniques including for example the use of factor $XIII^a$ inhibitors such as heavy metals (such as mercury), thiomerosal {[(o-carboxyphenyl) thio]ethyl mercury sodium salt}, inhibitory antibodies, or calcium chelators (since calcium is a necessary cofactor for the enzyme). Calcium chelators include, but are not limited to, EGTA (ethylenediaminetetra-acetic acid, ethylenglycolbis-(2-aminoethylether)tetra-acetic acid), and the like. For example, the converting enzyme is baxtroxobin used at a concentration of about 0.1 $\mu$g/ml to about 100 $\mu$g/ml, preferably to a concentration of about 0.5 $\mu$g/ml to about 50 $\mu$g/ml.

In FIG. 2, the substantive difference versus the procedure of FIG. 1 is that the solid support is added after the fibrin has been polymerized and removed.

In the exemplified schemes of FIGS. 1 and 2, the fibrinogen-converting enzyme is batroxobin ("Btx"), a proteinase from the snake venom of snakes of the genus Bothrops. Other proteinases of appropriate specificity can also be used. Snake venom proteinases are particularly suitable, including without limitation the venom enzymes from *Agkistrodon acutus, Agkistrodon contortrix contortrix, Agkistrodon halys pallas, Agkistrodon* (*Calloselasma*) *rhodostoma, Bothrops asper, Bothrops atrox, Bothrops insularis, Bothrops jararaca, Bothrops Moojeni, Lachesis muta muta, Crotalus adamanteus, Crotalus durissus terrificus, Trimeresurus flavorviridis, Trimeresurus gramineus* and *Bitis gabonica.*

The fibrinogen-converting enzyme is favorably coupled to a converting enzyme binding partner which will be used in an affinity procedure to reduce the concentration of the enzyme in a preparation. In the example, the converting enzyme binding partner is biotin, a member of the biotin-avidin binding pair, a pair of molecules that bind with extremely high affinity. An amino acid sequence for avidin is described in Dayhoff, *Atlas of Protein Sequence*, Vol. 5, National Biomedical Research Foundation, Washington, D.C., 1972 (see also, DeLange and Huang, *J Biol. Chem.* 246: 698–709, 1971), and an amino acid sequence for Streptavidin is described in Argarana et al., *Nucl. Acid Res.* 14:1871–1882, 1986. Nucleic acid sequences are available, for example, as follows: (1) chicken mRNA for avidin, Gene Bank Acc. No. X05343, Gore et al., *Nucl. Acid Res.* 15: 3595–3606, 1987; (2) chicken, strain White Leghorn gene for avidin, Gene Bank Acc. No. L27818 (3) streptavidin from *Strep. avidinii*, Gene Bank Acc. No. X03591, Argarana et al., *Nucl. Acid Res.* 14:1871–1882, 1986; (4) synthetic gene for streptavidin from *Strep. avidinii*, Gene Bank Acc. No. A00743, Edwards, WO89/03422; and (5) synthetic gene for streptavidin, Gene Bank Acc. No. X65082, Thompson et al., i Gene 136: 243–246, 1993.

Avidin and Streptavidin are preferably used in a tetrameric form, although monomers can be used. Other binding pairs that bind with high affinity include an antibody specific for a polypeptide or other molecule, any polypeptide to which an antibody is available or can be prepared, thioredoxin, which binds phenylarsine oxide (expression vectors include, for example, the thioredoxin fusion protein vector pTrxFus available from Invitrogen, Carlsbad, Calif.), poly-His sequences that bind to divalent cations such as nickel II (expression vectors include, for example, the pThioHis vectors A, B and C available from Invitrogen), glutathione-S-transferase vectors that bind to glutathione (vector for example available from Pharmacia Biotech, Piscataway, N.J.). Methods of producing such antibodies are available to those of ordinary skill in light of the ample description herein of polypeptide expression systems and of known antibody production methods. For antibody preparation methods, see, for example, Ausubel et al., *Short Protocols in Molecular Biology*, John Wiley & Sons, New York, 1992. Such extremely high affinity binding characteristics, while highly convenient, are not essential. Any affinity that can be used in an affinity-binding procedure to reduce the concentration of converting enzyme in a preparation can be used in this context. If the affinity procedure simply uses an antibody against the converting enzyme, then this aspect of the invention does not require a coupled converting enzyme binding partner, since the enzyme itself comprises the converting enzyme binding partner.

Unless the process is designed to prevention polymerization of fibrin monomer during the enzymatic conversion from fibrinogen to fibrin, the fibrin formed will polymerize into fibrin polymer, and thereby form a fibrin clot. Thus, in embodiments where the solid support with bound fibrinolysis-inhibiting protein remains after the addition of the fibrinogen converting enzyme, the desired fraction from the plasma comprises a solid clot and a solid support to which a fibrinolysis-inhibiting protein is bound. In the illustrated embodiment of FIG. 1, where the solid support is removed from the plasma prior to exposing the plasma to a fibrinogen-converting enzyme, the desired fraction is a solids fraction made up of fibrin polymer, which can include components which co-process with the fibrin polymer. These solids are collected, for instance by centrifugation or filtration. In some embodiments where the solids are made up of both the solid support (with bound fibrinolysis-inhibiting protein) and fibrin polymer, the conditions by which the fibrinolysis-inhibiting protein is eluted can be applied prior to the formation of fibrin monomer from the solid clot. Alternatively, the fibrin monomer can be prepared first, though care must be taken in selecting conditions for forming fibrin monomer that preserve the clot stabilizing activity of the fibrinolysis-inhibiting protein. Such conditions will vary depending upon the fibrinolysis-inhibiting protein that is to be isolated. Where the fibrinolysis-inhibiting protein is alpha-2-antiplasmin, care is preferably taken to limit the time or degree of exposure to low pH.

After the solids are isolated, fibrin monomer is recovered from the fibrin clot and, if the solid support (with bound fibrinolysis-inhibiting protein) is present, the fibrinolysis-inhibiting protein is dissociated from the inhibitor-binding ligand bound to the solid support. Fibrin monomer is recovered by adding a solubilizing agent to the fibrin clot. Such solubilizing agents can include, for example, acid solutions such as aqueous solutions having pH of about 5 or less, or chaotropic agents, such as urea, sodium bromide, guanidine hydrochloride, potassium cyanide, potassium iodide or potassium bromide. The solubilizing agents can be used at near the minimum concentration effective to maintain fibrin monomer (i.e., and fibrin-solubilizing effective amount). A number of conditions for forming fibrin monomer are described in Edwardson et al., European Patent Application No. EP 592,242.

A solid material having bound thereto a second binding partner, which is the complementary binding partner to the converting enzyme binding partner, is then added the fibrin monomer preparation to bind any converting enzyme as may continue to be found in the preparation. The solids, which, depending on the protocol used, can include (a) the solid material, (b) the solid support or (c) any residual fibrin clot material, is then removed, for instance by filtration or centrifugation.

The processed material can, depending on the procedure, comprise (1) a preparation containing fibrin monomer and the fibrinolysis-inhibiting protein, (2) separate preparations containing fibrin monomer and the fibrinolysis-inhibiting protein or (3) a preparation of fibrinolysis-inhibiting protein. Such processed materials can be stored in liquid form, for instance at about 4° C. or less, in frozen form, or as a dried form such as a lyophilizate. Lyophilizates are formed by standard methods. These lyophilizates are generally reconstituted in purified water or in a buffered aqueous solution. For the fibrin monomer, generally, the same solution composition of solubilizing agent previously used in the process can be used to reconstitute the lyophilizate. Or, if the user desires the fibrin to polymerize on reconstitution, an aqueous solution, which either (a) lacks a solubilizing agent or (b) is capable of reversing any solubilizing conditions carried in the lyophilizate, is employed.

As illustrated, to form fibrin sealants (i.e., clots) the fibrin monomer, a non-enzymatic polymerizing agent, and the fibrinolysis-inhibiting protein can be mixed together. The polymerizing agent is any reagent effective to reverse the conditions that prevent the polymerization of fibrin monomer. For example, if fibrin monomer is in an acidic solution, such as a 0.2 M sodium acetate, pH 4.0 solution, the polymerizing agent can be a basic solution, such as, without limitation, a solution of HEPES (N-[2-hydroxyethyl) piperazine-N'-[ethanesulfonic acid]), sodium hydroxide, potassium hydroxide, calcium hydroxide, bicarbonate buffers such as sodium bicarbonate and potassium bicarbonate, tri-metal salts of citric acid, salts of acetic acid and salts of sulfuric acid. Preferred alkaline buffers include: carbonate/bicarbonate; glycine; bis hydroxeythylaminoethane sulphonic acid (BES); hydroxyethylpiperazine propane sulphonic acid (EPPS); Tricine; morpholino propane sulphonic acid (MOPS); trishydroxymethyl aminoethane sulphonic acid (TES); cyclohexylaminoethane sulphonic acid (CBES); trishydroxymethyl aminoethane sulphonic acid (TES). The amount of alkaline buffer that is utilized should be enough to allow polymerization of the fibrin. It is preferred that about 10 parts to about one part of composition comprising fibrin monomer be mixed with about 1 part alkaline buffer. It is even more preferred that such ratio be about 9:1. The preferred ratio depends on the buffer, its concentration and pH and the desired concentration of the fibrin polymer. Where acidic pH is used as the solubilizing agent, preferably the fibrin solubilization occurs in the presence of calcium ions, such as at a concentration of about 20 mM.

In a particularly preferred embodiment, three streams of aqueous preparations are mixed to initiate a rapid clot formation process. These preparations are the fibrin monomer preparation, the fibrinolysis-inhibiting protein, and the non-enzymatic polymerizing agent. To allow the resulting gel-forming mixture to remain pliable for a sufficient period of time, the sealant mixture is generally formed either during the process by which the sealant is applied to its recipient surface, or within a few minutes prior to application. Generally, the sealant mixture remains conveniently pliable for about 30 seconds or less.

In a particularly preferred embodiment, the three streams are sprayed so that they converge and mix. Suitable spray heads are described in U.S. Pat. Nos. 5,605,541, 5,376,079, and 5,520,658 and PCT Application 97/20585.

2. Secondary Binding Protocols

Figure 2:
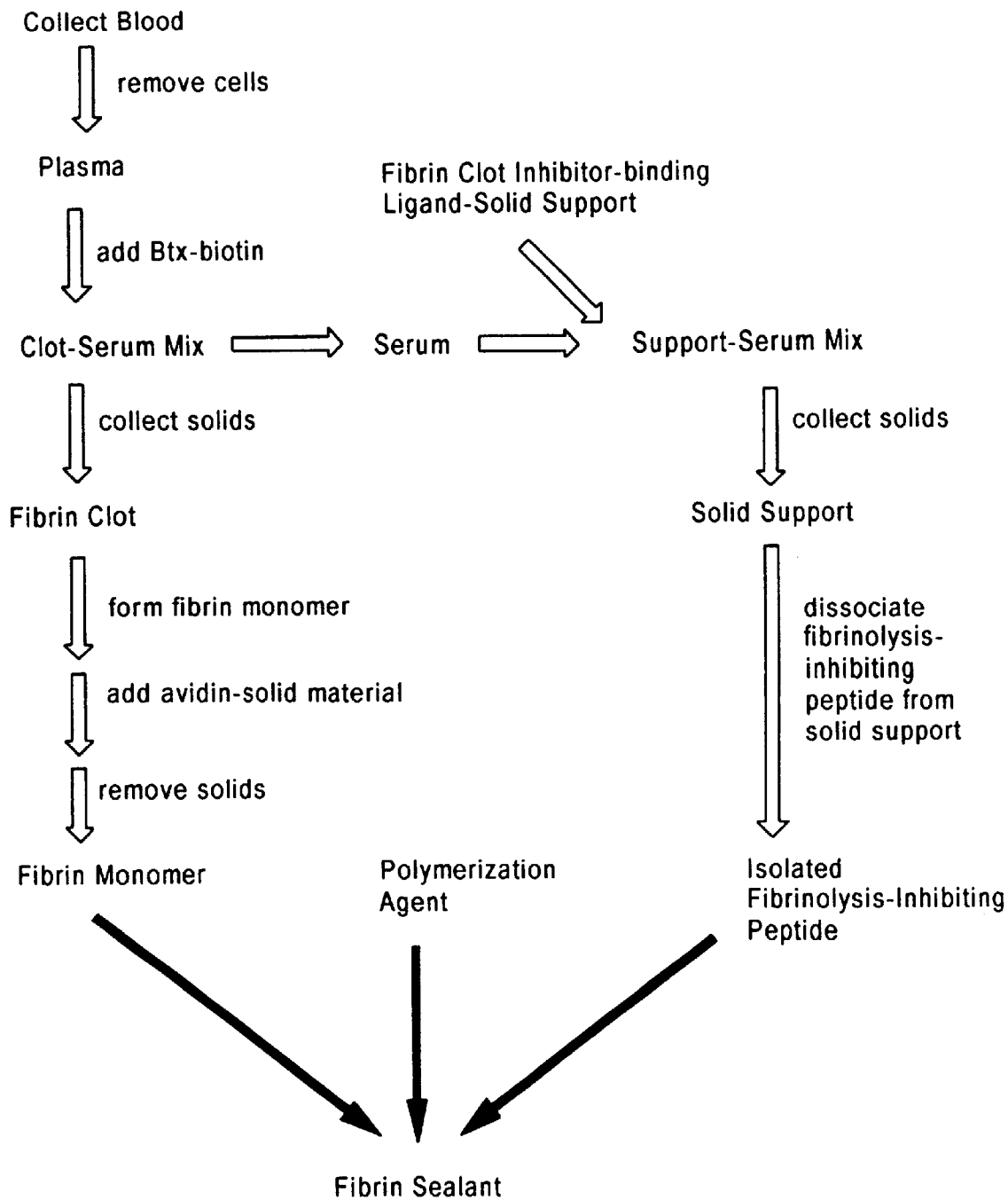
FIG. 2 shows an outline of a procedure for preparing a fibrin sealant containing an autologous fibrinolytic inhibitor, where the inhibitor is removed from post-polymerization serum.
Figure 3:
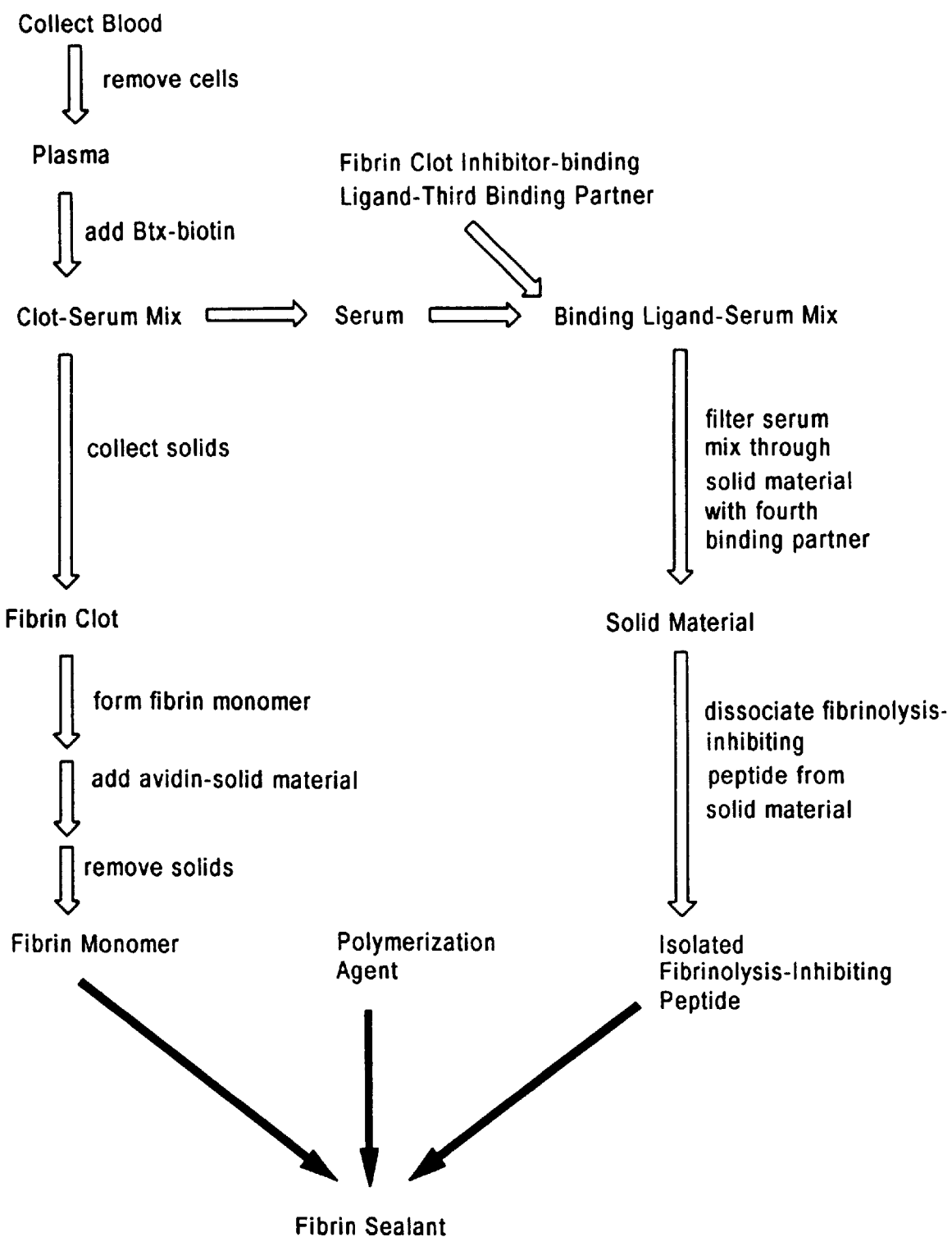
FIG. 3 shows an alternative procedure where the autologous fibrinolytic inhibitor in a serum or plasma is first bound to an affinity ligand in the solution phase.

In some embodiments, the fibrin clot inhibitor-binding ligand can have attached to it (1) a third binding partner or other which is a member of a high affinity binding pair, or (2) another extraction implement. In this way, the fibrin clot inhibitor-binding ligand can be contacted with the plasma or serum under solution conditions, and then the fibrinolysis-inhibiting protein isolated for instance by contacting plasma or serum with a solid material to which is bound the other member of the high affinity binding pair (the fourth binding partner). FIG. 3 illustrates such an embodiment which is analogous to that of FIG. 2. Instead of adding a fibrin clot inhibitor-binding ligand-solid support to the serum, a fibrin clot inhibitor-binding ligand, to which a third binding partner is attached, is added. A solid material to which is attached the fourth binding partner is then used to remove the a fibrinolysis-inhibiting protein from the serum. In the illustration, the serum is filtered through the solid material, though other forms of contacting are of course available.

All of the illustrated purifications indicate that the isolated fibrinolysis-inhibiting protein and the fibrin monomer are kept separately prior to forming the fibrin sealant. In a preferred embodiment, these components are kept separately. However, the invention is not so limited; for example, where the fibrin monomer and the fibrinolysis-inhibiting protein are lyophilizates or otherwise in a dry form, it is convenient to store the two components together.

C. Preparation of Solid Supports and Solid Materials

The solid support or solid material to which inhibitor-binding ligands and second binding partners, respectively, are bound are most preferably particles of carbohydrate-based material such as agarose, cross-linked agarose or cross-linked dextran. The term "solid material" is used herein to refer to the same types of solids as the term "solid support", but the separate terms are used herein to accentuate the difference in the types of affinity ligands bound thereto. Most often it is anticipated that the molecule to be bound to solid support or solid material will be a polypeptide, for which the most convenient functionality for covalent coupling is often an amino or thio moiety on the polypeptide. Methods for covalently coupling molecules to solid supports or solid materials are well known in the art, and include for example creating reactive sites on the solid supports or solid materials with cyanogen bromide or reacting the solid supports or solid materials with bifunctional reagents such as diglycidyl ethers. See, for example, "Attachment to Solid Supports" in Means and Feeney, *Chemical Modification of Proteins*, Holden-Day, San Francisco, 1971, pp. 40–43 or *Affinity Chromatography: A Practical Approach*, Dean et al., eds., IRL Press, Oxford, 1991. For coupling with silica-based materials, alkyloxysilane moieties, for example, can provide the silica-reactive moiety of a bifunctional coupling reagent. For example, γ-glycidoxypropyltrimethoxy-silane can be reacted with the silica-based material, which is then either directly reacted with the protein (via the glycidic ether moiety), or a second step is employed such as reacting the glycidic ether with an amine and subsequently attaching by reductive alkylation a glycoprotein that is mildly oxidized (for instance with periodate) to contain aldehyde moieties. A preferred coupling chemistry reacts a carbohydrate-based solid support with a hydrazide group, and then couples by reductive alkylation a glycoprotein that has been mildly oxidized (for instance with periodate) to contain aldehyde moieties. See, Axelsson et al., *Thromb. Haemost.* 36: 517, 1976.

D. Interaction With Solid Support

Preferred solution conditions for associating the fibrinolysis-inhibiting protein with the solid support containing bound inhibitor-binding ligand include the use of an aqueous buffer, a substantially neutral pH. The temperature at which the fibrinolysis-inhibiting protein and the solid support are contacted is preferably between about 0° C. and about 40° C. It is not necessary in the methods of the invention that all of the fibrinolysis-inhibiting protein in a starting material be associated with the solid support, however, it is desirable that a sufficient amount be associated to provide for clot stabilization. Accordingly, for example, with most body fluids containing alpha-2-antiplasmin, sufficient association can be anticipated within minutes of the initial contact between the fluid and the solid support containing bound AP-binding ligand. The plasma producing the fibrinolytic inhibitor is, in a preferred embodiment, about the same amount of plasma as used to produce the fibrin of the sealant.

Useful reagents for destabilizing the interaction between the inhibitor-binding ligand bound to the solid support and the fibrinolysis-inhibiting protein include substances that compete for binding the fibrinolysis-inhibiting protein such as, for alpha-2-antiplasmin, AP-binding ligands that are not bound to the support, such as lysine, 6-aminohexanoic acid, and other lysine analogs. For example, the elution solution can be 10 mM of such a lysine analog in the presence of an appropriate buffer and sufficient salt (such as 0.5 M NaCl) to minimize non-specific adsorptions to the solid support.

In one embodiment, the conditions that effect the dissociation of the fibrinolysis-inhibiting protein from the inhibitor-binding ligand bound to the solid support preferably allow the interaction between the converting enzyme binding partner and the second binding partner. In this way, the second binding partner, bound to the solid material, can be used to remove residual converting enzyme without the need to (a) remove the solid support and (b) modify conditions to favor the interaction between the converting enzyme binding partner and the second binding partner.

E. Creation of Alternative AP-binding Ligands

The Kringle regions of plasminogen serve as models for the design of alternative AP-binding ligands. The Kringle 1 region of human plasminogen, corresponding to residues 84 through 162, is a particularly useful model. One design approach is the Multipin Synthetic Peptide System described by Beysen et al., *J. Immunol. Methods* 102: 259, 1987. Under this approach, for instance, numerous polypeptides having a relationship with one of the Kringle regions can be synthesized in a form attached via a polyethylene/polypropylene linkers to the surface of the wells of a microtiter plate. The affinity of these surface-bound peptides for alpha-2-antiplasmin can be determined using labeled alpha-2-antiplasmin. Such binding assays will typically include treatments of the solid surface to reduce non-specific binding, the use of polypeptides that are not related to a Kringle region to indicate the level of non-specific binding, and the use of established AP-binding ligands such as plasminogen to confirm that the assay is operative.

Further techniques for identifying AP-binding moieties can include, for example, the combinatorial chemistry procedures described by Fodor et at., "Very Large Scale Immobilized Polymer Synthesis," WO 92/10092. Alternatively, phage display technology, wherein recombinantly produced diversity libraries of polypeptides are presented on the surface of a phage, can be used. The phages selected for their ability to bind alpha-2-antiplasmin can be grown and the relevant portion of their genome sequenced to identify polypeptides with binding potential. Such phage display technology is described patent documents belonging to Dyax Corporation of Cambridge, Mass., including Robert Ladner et al., U.S. Pat. No. 5,223,409 (Directed Evolution of Novel Binding Proteins) and U.S. Pat. No. 5,403,484 (Viruses Expressing Chimeric Binding Proteins).

F. Miscellaneous Aspects

When body fluids are used as the source for fibrin, in many cases it will be desirable to isolate with the fibrin ancillary factors such as factor XIII or factor XIII$^a$ and thrombin. When purification techniques are used that isolate fibrin via the reversible formation of a fibrin polymer, it is believed that the fibrin polymer has affinity for a number of such ancillary factors, such that the isolated product will retain these factors. In some cases, it will be desirable to limit the amount that non-fibrin materials are washed out of the fibrin polymer, for instance, by limiting the degree to which the fibrin polymer is compressed in the course of a method according to the invention, in order to assure the co-isolation of sufficient amounts of ancillary factors.

The present invention can be used for treating any animal having a fibrin-based system for controlling bleeding, but is preferably used for treating mammals, most preferably humans.

The following examples further illustrate the present invention, but of course, should not be construed as in any way limiting its scope.

EXAMPLE 1

Preparation of Plasminogen Fragments and Attachment of AP-binding Ligands to Cross-linked Agarose Proteolytic fragments of plasminogen were produced to provide AP-binding ligands. The fragments were prepared as described by Sottrup Jensen, Claeys, Zajdel, Petersen and Magnusson, *Progress in Chemical Fibrinolysis and Thrombolysis*, 3: 191–209, 1978. Plasminogen fragments were attached to agarose supports as described by Wiman, *Biochemnistry J* 191: 229–232, 1980.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of forming a fibrin sealant from plasma comprising:
    (a) contacting the plasma, which contains alpha-2-antiplasmin, with an extraction implement that has both an alpha-2-antiplasmin-binding ligand and a first binding partner that is a member of a binding pair that comprises the first binding partner and a second binding partner, which partners bind to each other with an association constant of at least $10^5$ $M^{-1}$;
    (b) isolating, from the plasma, the alpha-2-antiplasmin bound to the extraction implement;
    (c) contacting the plasma, which contains fibrinogen, with a fibrinogen-converting enzyme to form fibrin polymer and serum;
    (d) isolating from the plasma and acid solubilizing the fibrin polymer to form a first composition comprising acid-solubilized fibrin monomer; and
    (e) creating a fibrin sealant kit comprising, separately packaged, the first composition in an amount sufficient to form a clot, and a second composition comprising alpha-2-antiplasmin eluted from the isolated extraction implement in an amount sufficient to stabilize at least a clot-forming effective amount of the second composition,
    wherein the alpha-2-antiplasmin is isolated from the plasma prior to step (d).

2. The method of claim 1, wherein alpha-2-antiplasmin-binding ligand comprises one or more Kringle domains effective to bind alpha-2-antiplasmin.

3. The method of claim 1, wherein the first binding partner is a member of a binding pair, the members of which bind to each other with an association constant of at least $10^6$ $M^{-1}$.

4. The method of claim 1, further comprising (1) sealing a tissue to prevent fluid loss or to prevent adhesions to the tissue or (2) coating a material to increase its biocompatibility by:
    (e) contacting the first composition with a polymerizing agent composition effective to convert the fibrin monomer preparation into a fibrin clot; and
    (f) further contacting the first composition with a clot preserving effective amount of the second composition.

5. The method of claim 1, wherein the members of the binding pair bind to each other with an association constant of at least $10^6$ $M^{-1}$.

6. The method of claim 1, wherein the members of the binding pair bind to each other with an association constant of at least $10^7$ $M^{-1}$.

7. A method of forming a fibrin sealant from an animal and sealing a tissue to prevent fluid loss or to prevent adhesions to the tissue comprising:

(1) collecting plasma, which contains both alpha-2-antiplasmin and fibrinogen, from an animal;

(2) contacting the plasma with an extraction implement that has both an alpha-2-antiplasmin-binding ligand and a first binding partner which is a member of a binding pair that comprises the first binding partner and a second binding partner, which partners bind to each other with an association constant of at least $10^5$ $M^{-1}$;

(3) collecting the extraction implement by binding the first binding partner to the second binding partner, which is attached to a support and separating the support from the plasma;

(4) isolating, from the extraction implement, alpha-2-antiplasmin;

(5) contacting the plasma with a fibrinogen-converting enzyme to form a fibrin polymer and serum;

(6) isolating from the plasma and acid solubilizing the fibrin polymer to form a sealant composition comprising acid-solubilized fibrin monomer;

(7) contacting the isolated alpha-2-antiplasmin from step (4) with the sealant composition with a non-enzymatic agent to polymerize the fibrin and form a fibrin clot, wherein the amount of $\alpha 2$-antiplasmin is sufficient to stabilize the clot; and (8) contacting the tissue of the animal with the clot, wherein the alpha-2-antiplasmin is removed from the plasma prior to the isolation of step (6).

8. The method of claim 7, wherein alpha-2-antiplasmin-binding ligand comprises one or more Kringle domains effective to bind alpha-2-antiplasmin.

9. The method of claim 7, wherein the first binding partner is a member of a high affinity binding pair, the members of which bind to each other with an association constant of at least $10^6$ $M^{-1}$.

10. The method of claim 7, wherein the first binding partner is a member of a high affinity binding pair, the members of which bind to each other with an association constant of at least $10^7$ $M^{-1}$.

* * * * *